United States Patent
Knight et al.

(10) Patent No.: US 7,527,625 B2
(45) Date of Patent: May 5, 2009

(54) TRANSPARENT ELECTRODE FOR THE RADIOFREQUENCY ABLATION OF TISSUE

(75) Inventors: Bradley P. Knight, Evanston, IL (US);
Larry Blankenship, Boulder, CO (US);
John H. Hanlin, Louisville, CO (US);
David C. Amundson, Boulder, CO (US)

(73) Assignee: Olympus Corporation, Tokyo (JP)

( * ) Notice: Subject to any disclaimer, the term of this patent is extended or adjusted under 35 U.S.C. 154(b) by 708 days.

(21) Appl. No.: 10/912,732

(22) Filed: Aug. 4, 2004

(65) Prior Publication Data
US 2006/0030844 A1 Feb. 9, 2006

(51) Int. Cl.
*A61B 18/18* (2006.01)

(52) U.S. Cl. .......................... 606/45; 606/41
(58) Field of Classification Search ............... 606/27–50
See application file for complete search history.

(56) References Cited

U.S. PATENT DOCUMENTS

| | | | | |
|---|---|---|---|---|
| 4,232,676 | A * | 11/1980 | Herczog | 606/50 |
| 5,722,403 | A * | 3/1998 | McGee et al. | 600/373 |
| 5,759,150 | A * | 6/1998 | Konou et al. | 600/114 |
| 5,871,481 | A * | 2/1999 | Kannenberg et al. | 606/34 |
| 5,873,877 | A * | 2/1999 | McGaffigan et al. | 606/41 |
| 5,916,233 | A * | 6/1999 | Chin | 606/190 |
| 6,059,726 | A * | 5/2000 | Lee et al. | 600/439 |
| 6,080,102 | A * | 6/2000 | Konou et al. | 600/114 |
| 6,086,586 | A * | 7/2000 | Hooven | 606/50 |
| 6,394,949 | B1 * | 5/2002 | Crowley et al. | 600/127 |
| 6,451,009 | B1 * | 9/2002 | Dasilva et al. | 606/12 |
| 6,592,582 | B2 * | 7/2003 | Hess et al. | 606/49 |
| 6,918,906 | B2 * | 7/2005 | Long | 606/41 |
| 2001/0027316 | A1 * | 10/2001 | Gregory | 606/15 |
| 2002/0147447 | A1 * | 10/2002 | Long | 606/41 |
| 2003/0065271 | A1 * | 4/2003 | Khoury | 600/509 |
| 2003/0208123 | A1 * | 11/2003 | Panescu | 600/431 |

OTHER PUBLICATIONS

WO/2000/24310 (Amundson et al) May 4, 2000, pp. 2-3 and 6-7.*

* cited by examiner

*Primary Examiner*—Michael Peffley
(74) *Attorney, Agent, or Firm*—Scully, Scott, Murphy & Presser, P.C.

(57) ABSTRACT

A novel transparent electrode that uses a conductive coating to allow delivery of current to the heart as well as outward imaging through the electrode is described. The embodiments disclose a catheter incorporating an endoscope, whose imaging tip is coated with a conductive coating that is transparent in the endoscopic image. However, a transparent electrode may be fashioned for any imaging modality, such as intracardiac echocardiography (ICE), that finds the electrode to be transparent to the energy used. This electrode coating may be a thin, optically transparent or translucent coating of platinum or gold or may be a pattern with enough open spaces to see the underlying tissue, such as looking through a screen. A wire is connected to the conductive coating and routed to a radiofrequency generator.

9 Claims, 10 Drawing Sheets

Close-up of Gold Stripe Pattern on Hood Connected to Tab

Figure 1: Schematic Diagram of Infrared Endoscope System

Figure 2: Distal end of Endoscope

Figure 3: Gold coated Infrared Endoscope-Ablation Catheter

Figure 4: Close-up of Gold Stripe Pattern on Hood Connected to Tab

Figure 5: Gold Stripe Pattern Infrared Endoscope-Ablation Catheter

Figure 6: Rigid Endoscope with Gold Coating Ablating Liver Tumor

Figure 7: Gold Coated Hood with a Coated Dissimilar Metal Forming Thermocouple

Figure 8: Half- hemisphere Hood Coating with Two Dissimilar Metals

Figure 9: Infrared Endoscopic View of Half-Hemisphere Ablation Electrode Against Tissue Figure 10: Alternate Ablation Patterns Deposited on Hood

TRANSPARENT ELECTRODE FOR THE RADIOFREQUENCY ABLATION OF TISSUE

BACKGROUND OF THE INVENTION

This invention relates to radiofrequency ablation of human tissue, particularly heart tissue for the elimination of arrhythmias.

The following references provide useful background material to the present invention, and are all incorporated herein by reference.

| Patent References: | | |
| --- | --- | --- |
| Kushihashi | 12/1969 | 3,484,263 |
| Levy | 6,1970 | 3,515,571 |
| Avitall | 1/1996 | 5,487,385 |
| Swanson | 12/1996 | 5,582,609 |
| Swartz | 12/1998 | 5,846,223 |
| Shearon | 7/1999 | 5,919,188 |
| Haissauguerre | 5/2000 | 6,064,902 |
| Amundson | 1/2001 | 6,178,346 |
| O'Brian | 1/2001 | 6,168,825 |
| Suorsa | 3/2001 | 6,206,831 |
| Webster | 4/2001 | 6,210,406 |
| Tu | 5/2001 | 6,238,390 |
| Gaiser | 6/2001 | 6,241,728 |
| Stewart | 12/2001 | 6,325,797 |
| Sutton | 9/2002 | 6,443,950 |
| Amundson | 11/2002 | PCT/US02/361; PCT/US02/364 |
| Other References | | |
| Knight | 5/2004 | Heart Rhythm 2004 Abstract 26 |

Lardo et al. "Visualization and Temporal/Spatial Characterization of Cardiac Radiofrequency Ablation Lesions using Magnetic Resonance Imaging" Circ 2000: 102: 698-705

In the field of cardiology, arrhythmias (irregularities in heart rate) are increasingly being treated by a procedure called catheter ablation. In catheter ablation, a catheter is inserted, usually from the femoral veins, into the right heart of a patient, where it is critically positioned to ablate spots in the heart, thought to be propagating the arrhythmia. If the ablation is successful, the arrhythmia is permanently disrupted and the patient no longer requires conventional therapy such as drugs or implanted devices such as pacemakers or defibrillators. For example, aberrant conduction pathways between atria and ventricles create some pathological high heart rates, called supraventricular tachyarrhythmias (SVT's). These pathways are detected by mapping electrical potentials with multi-electrode catheters in the atrium. Once located, a small radio-frequency burn of about 10 square millimeters is created, electrically ablating the pathway.

A conventional RF ablation catheter contains a platinum hemisphere on the distal end of the catheter. The electrode is about 2.3 mm in diameter and from 4-10 mm in length. Ablation occurs in tissue because the radiofrequency energy heats the intracellular fluid inside the cell, causing the cell to desiccate. It is very difficult to determine how much of the catheter electrode is in contact with the tissue since catheter electrodes and probes are cylindrical and the heart tissue cannot be visualized clearly with existing fluoroscopic technology. Further, because of the cylindrical shape, some of the exposed electrode or probe area will almost always be in contact with blood circulating in the heart, giving rise to a risk of clot formation.

Clot formation is frequently associated with RF energy inside the heart because it is difficult to prevent the blood from being exposed to the electrode or probe surface. Some of the RF current flows through the blood between the electrode and the heart tissue and this blood is coagulated possibly resulting in clot formation. When RF energy is applied, the temperature of the electrode is typically monitored so as to not exceed a preset level, but temperatures necessary to achieve tissue ablation frequently results in blood coagulum forming on the electrode. Overheating of tissue is a major complication, because the temperature monitoring only gives the temperature of the electrode or probe, which is being cooled on the outside by blood flow. The actual temperature of the tissue being ablated by the electrode or probe can be considerably higher than the electrode or probe temperature, and this can result in overheating, or even charring, of the tissue. Overheated or charred tissue can act as a locus for thrombus and clot formation. When applied to the left heart as in atrial fibrillation eradication, the thrombus can lead to strokes and heart attacks.

The electrode temperature is only an indirect measure of the complex temporal and spatial temperature at the electrode-tissue interface. It can significantly underestimate the temperature at the tissue interface because of cooling effect of flowing blood. It provides only an average temperature of the blood and tissue contacting the electrode with no information concerning the spatial temperature profile. The relatively large thermal mass of the electrode delays the temperature changes occurring at the electrode-tissue interface. Ideally, a multitude of discrete thermocouples or other temperature measuring devices on the electrode surface would provide a much better measure of the tissue and blood temperature properties.

More common arrhythmias such as atrial fibrillation, flutter and more potentially lethal arrhythmias such as post-myocardial-infarct ventricular tachycardia require lines to be burned instead of "spots". Atrial fibrillation is the most common arrhythmia in man, affecting over 3 million people in the United States. In this arrhythmia, the atria quiver; no longer pumping blood, and an unstable heart rate is a side feature. Patients with AF are much more prone to stroke, congestive heart failure, myocardial infarctions and fatal ventricular arrhythmias. Patients can be in temporary (paroxysmal) atrial fibrillation or permanent atrial fibrillation (most dangerous). Atrial flutter, often a precursor to atrial fibrillation, is a fluttering of the atria, also with loss of atrial mechanical function. It has a prevalence ranging from 1 in 81 to 1 in 238 hospitalized patients. This arrhythmia is usually disabling and resistant to antiarrhythmic drugs and it carries a potential risk of thromboembolism and cardiomyopathy. Post-myocardial-infarct ventricular tachycardia occurs following a myocardial infarction. The infarct sometimes results in short-circuiting of the ventricular electrical activation pattern, resulting in tachycardia. It is a frequently lethal tachycardia and as a result is the principle indication for receiving an implantable defibrillator.

Unlike SVT's, ablation lines, rather than spots, need to be created to eradicate these arrhythmias, based on anatomical considerations rather than electrical potentials. For atrial fibrillation, lines circling the pulmonary veins and sometimes-additional lines seem to be effective for the eradication of the arrhythmia. For atrial flutter, a linear ablation around the tricuspid annulus and Eustachian valve and ridge on the septum is effective in terminating the arrhythmia. For post-myocardial-infarct ventricular tachycardia, a circular ablation around the infarct is sometimes successful in eradicating the arrhythmia.

Since these procedures are performed without local visualization, the location of the burns cannot be seen; making connection of the spots very difficult. As stated in Lardo et al.

Visualization and Temporal/Spatial Characterization of Cardiac Radiofrequency Ablation Lesions using Magnetic Resonance Imaging Circ 2000: 102:698-705, "... There is general agreement that new approaches to facilitate anatomy-based catheter ablation are needed"

Catheter ablation of atrial fibrillation is currently accomplished by accessing the left atrium through a needle puncture from the right atrium, and placing circular lesions around the pulmonary veins. Various circular burn configurations have been evaluated, ranging from encircling all of the pulmonary veins to encircling each one individually. Some protocols also advocate the placing of additional linear lesions between the pulmonary vein and the mitral valve. A dangerous complication of this procedure is stenosis of the pulmonary veins from ablations too far inside the pulmonary veins.

Various ablation catheters have been developed which attempt to produce continuous lesions. Avitall (U.S. Pat. No. 5,487,385), Kroll (U.S. Pat. No. 6,287,306), Tu (U.S. Pat. No. 6,241,728 ) and Shearon (U.S. Pat. No. 5,919,188) disclose catheters thought to produce linear lesions. Sutton (U.S. Pat. No. 6,443,950) and Swartz (U.S. Pat. No. 5,846,223) disclose catheters, which are intended to produce continuous lesions for atrial flutter eradication. Catheters capable of forming linear circular lesions, needed for pulmonary vein isolation, are disclosed by Haissauguerre (U.S. Pat. No. 6,064,902), Tu (U.S. Pat. No. 6,241,728), Stewart (U.S. Pat. No. 6,325,797) and Gaiser (U.S. Pat. No. 6,241,728). All of these catheters rely on spatial configurations to orient the catheter in close proximity to the targeted the tissue and electrode separations small enough so that the individual lesions form one continuous lesion. For example, Stewart (U.S. Pat. No. 6,325,797) teaches a catheter of closely spaced electrodes where the distal end assumes a circular configuration for placement around a pulmonary vein. Haissauguerre (U.S. Pat. No. 6,064,902) teaches a pulmonary vein ablation catheter which is inserted into the pulmonary vein and rotated during ablation to produce a linear lesion.

In general, these linear-lesion producing catheters have two problems: variations in cardiac anatomy and inability to assess lesion production. If the cardiac area to be ablated conforms to the shape of the lead and all of the ablation electrodes are in intimal contact with the tissue, a linear lesion at the proper location should be formed. However, there is great variation in cardiac anatomy among patients. For example, most patients have four pulmonary veins, however some patient's have more veins. Some patients have pulmonary veins in close proximity to each other rather than being spatially separate. If a circular configured catheter, such as Stewart (U.S. Pat. No. 6,325,797), were used in pulmonary veins in close proximity to each other, some of the electrodes might actually reside in the neighboring pulmonary vein, possibly causing pulmonary vein stenosis.

Producing a continuous lesion by connecting individual spot lesions is also somewhat speculative, since the contact pressure against tissue determines the size of the lesion. Catheter configurations such as Swanson (U.S. Pat. No. 5,582,609), which form a linear lesion from the connection of small circular lesions, use electrode separations that produce a linear lesion if the electrodes are lying against tissue. If an electrode is not lying against tissue, a much smaller lesion or no lesion will be formed, leaving a corresponding gap in the linear lesion. Gaps in linear lesions may actually worsen the arrhythmogenic condition, such as in atrial flutter ablation, where gaps in the lesion can lead to atrial fibrillation.

The difficulty of making continuous lesions with radiofrequency energy has led to the exploration of other ablation sources. Sources such as lasers, microwaves, ultrasonic energy and freezing have all been proposed by investigators as a means of making linear lesions. The safety and efficacy of these approaches is still unclear. For example, laser ablation is a common technique in other areas of medicine, where it is possible to image the effects of the ablation. When performed blindly, however, laser ablation can lead to perforation of a cardiac chamber.

Intracardiac echocardiography uses ultrasound to indirectly visualize the heart and electrode tissue interface during catheter ablation procedures. This imaging technique is limited by the need for an additional catheter to be placed in the heart. In addition it is limited by the need for frequent repositioning of the intracardiac echo catheter in order to keep the tip of the ablation catheter within the field of view. Cardiac motion makes continuous imaging of the interface between the ablation electrode and the endocardium difficult. As a separate catheter, the ICE catheter can practically only be positioned in the near vicinity of the ablation catheter. Suorsa (U.S. Pat. No. 6,206,831) discloses a more sensitive ultrasound means of evaluating tissue contact by having the ultrasound transducers adjacent to each of the electrodes. The patent assumes that if the electrodes have a certain separation and the ultrasonic transducers verify tissue contact, then a continuous lesion will result. There is no discussion of imaging through the electrode tip to provide close proximity images of the tissue surface.

Recently, a technique called infrared endoscopy has been developed, using near-infrared light of creating a direct image of structures through blood by Amundson (U.S. Pat. No. 6,178,346). This device illuminates tissue with infrared light. The patent discusses and makes claims for illuminating structures obscured by blood with infrared illumination and recording the reflected image in an infrared camera. Illumination wavelength candidates must be in a local absorption minimum such as: 800-1350 nm, 1550 nm-1850 nm and 2100 nm-2300 nm. With this system, high-resolution, real-time images of lesion production are possible. Although the patent discusses the imaging of catheter ablation procedures, it does not consider the possibility of constructing the ablation electrode on the endoscope.

The infrared endoscope described in U.S. Pat. No. 6,178, 346 contains on its distal end a focusing lens and a hood covering the distal end. The hood is the interface between blood, illumination, and receiving optics in their catheter configurations. One preferred hood embodiment appears as a transparent hemispheric structure extending about 2-4 mm from the optical fibers on the distal end of the catheter. The hoods can be made from various materials including glass, hardened adhesives, polymers, fused silica, and acrylic.

A U.S. patent application was also filed by Amundson, et. al. which applied the infrared endoscope to ablation. The Amundson application teaches means of orienting an extendable ablation electrode so that it is preferentially in contact with tissue instead of blood, guided by visual feedback from the infrared endoscope.

The process of coating a substrate with a transparent or semi-transparent metallic coating has existed for decades. Levy (U.S. Pat. No. 3,515,571) and Kushihashi (U.S. Pat. No. 3,484,263) in 1969-70 describe means of applying thin semi-transparent gold films unto substrates such as glass. O'Brien (U.S. Pat. No. 6,168,825) in a recent patent describes more advanced techniques.

Utilization of a metallic deposit as an ablation electrode has other imaging ramifications. Magnetic resonance (MR) imaging is an alternative to fluoroscopy and has many advantages including soft tissue recognition and no ionizing radiation. Unfortunately, MR imaging is incompatible with conventional ablation catheters due to the powerful magnets in the MR imager. A magnetic material such as stainless steel and platinum (used for the wire connection and electrode in conventional ablation catheters) can be moved or heated by the MR magnets. Only materials with negligible or no para or ferro-magnetism are MR-compatible. Non-magnetic materials include gold, nitinol and titanium. Copper has also been used as a wire material because of its small magnetic properties. The amount of heating and catheter movement on magnetic materials is proportional to the mass of magnetic material in the catheter. When an ablation electrode is formed by coating a non-metallic substrate with a para or ferro-magnetic coating of thickness 20-100 nm, the electrode mass is insignificant and as a result the overall magnetic properties are negligible.

SUMMARY OF THE INVENTION

An inventor of this patent is a cardiologist specializing in electrophysiology and has used infrared endoscopy to view the creation of RF lesions in the heart in a series of canine experiments. In these experiments, the endoscope was positioned in close proximity to the electrode of the ablation catheter. This close-proximal positioning of the individual catheters was very time consuming and once achieved, the resulting image contained motion artifact and the ablative tissue region was sometimes unrecognizable due to varying angles and distances between the two catheters. The image acquired by the endoscope showed the ablation electrode as a large, highly reflective surface occupying a significant area in the image. As RF energy was applied to the electrode, interesting phenomena such as bubble and coagulum formation were observed as well as a brightening of the tissue immediately adjacent to the electrode corresponding to lesion formation. Difficulties in viewing the underlying tissue included:
1. Images of most of the ablated region could not be seen because the electrode obscured much of the region.
2. The surface glare of the bright metal electrode obscured tissue detail in the immediate vicinity of the electrode.
3. Motion artifact from the heart and respiratory cycles between the endoscope and the ablation catheter obscured tissue detail.
4. Variable angles and distances between the endoscope and ablated tissue sometimes prevented the tissue to be seen in sufficient detail.

The difficulties associated with a separate endoscope or other catheter dedicated to imaging during ablation procedures can be overcome by coupling the endoscope or other imaging tool to the ablation catheter by viewing through an ablation electrode that is transparent to the imaging technique. Electrodes can be manufactured to be optically transparent using the technique of applying metallic films onto substrates using methods such as sputtering. The formation of metallic films has a long history, particularly in the application of gold, silver, platinum and indium-titanium oxide films. These films can be easily applied to non-metallic surfaces, such as glass or silica. Thin metallic films are particularly interesting material for ablation electrodes because of the following properties:
1. Metallic coating deposits contain so little metal that the para and ferro-magnetic properties of the metal are negligible and thus compatible with magnetic resonance imaging. In addition, gold has no para or ferro-magnetic properties.
2. They can easily be applied to non-metallic substrates such as glass or silica in thin layers of tens of nanometers.

It is easy to deposit gold in any pattern desired. Unlike conventional platinum electrodes, which consist of a structurally solid platinum hemisphere, gold can be applied in any configuration to a non-metallic substrate.

This invention teaches methods and means of constructing a transparent ablation electrode whereby the underling tissue can be imaged during the ablation using metallic film deposition technology applied to transparent non-metallic substrate. Transparent or "substantially transparent" as used herein means sufficiently transparent so that a particular imaging modality can be used. The invention also teaches the methods and means of constructing thermocouples on the electrode surface using the electrode surface as one of the thermocouple metals. Adding another deposition of a dissimilar metal under the electrode deposition creates a thermocouple on the electrode surface. The two metals are electrically connected (coupled) such by their physical connect or other means. Low-thermal-mass thermocouples can be created at one or more points on the surface to more accurately measure surface temperature with much smaller time delays than conventional ablation catheters. The temperature derived from these thermocouples can be used to more precisely control the output of RF generators to form more consistent lesions and minimize complications. The thermocouples may also be transparent to the imaging function.

This invention teaches novel methods and means of displaying temperature information in a user-friendly format. It also teaches alternate means of measuring temperature in conjunction with an endoscope. In addition, it teaches methods and means of constructing complex electrode patterns on the ablation electrode surface to create alternate ablation patterns. The invention also teaches methods and means of constructing a magnetic resonance imaging compatible ablation catheters using thin metallic depositions on a non-metallic substrate connected to a gold, titanium or nitinol wire routed to the catheter distal end.

This invention permits the entire ablation region to be visualized by incorporating over the imaging transducer a transparent ablation electrode and one or more connecting wires, which run to the proximal end of the endoscope for insertion into an RF generator. This can be accomplished in two ways:
1. Coat the transducer with a solid but very thin metallic coating, such as gold. In the case of an ICE catheter, the coating must be thin enough to permit substantial transmission of high frequency sound waves. For light endoscopes or OCT catheters, a sub-100 nanometer coating will be about adequately transmissive, allowing around half the light to illuminate tissue, with half internally reflected within the hood. The reflected light is mostly eliminated using a single-point offset correction (SPOC) feature, found on many infrared cameras. The SPOC removes persistent reflections from the overall scene by subtracting a reference image from the actual frame on a frame-by-frame basis. Other possible conductive coatings include platinum, silver, indium-titanium-oxide and any other conductive coating, which can be made semi-transparent. The endoscope already contains a clear hemispheric or other rounded shaped dome, called a hood. The hood can be glass, silica, acrylic or other polymeric. Glass is one of the preferred substrates for metallic coatings. If this hood is now coated with a thin metallic film it also becomes an ablation electrode. Most of these materials can have conductive coatings applied to their smooth surfaces using several coating technologies. Typically, applying the evaporated metal film in a vacuum is the preferred method because of enhanced binding at the molecular level. The other methods of dipping, spraying, and painting will coat the surface but may not reach the adherence requirement to survive modern sterilization techniques and passage through hemostasis valves. For the purposes of this discussion vacuum metal coating will be used.

2. Coat metallic patterns on the imaging transducer with open spaces, so that the open space is sufficient to make the electrode appear semi-transparent. The pattern would be electrically connected and contain a connection for a wire routed to the distal end of the catheter. A suitable ratio of open surface area to metallic surface area would probably range from 0.2-0.8. The stripe pattern is reduced by the SPOC to a neutral contrast, leaving only the tissue as a multi-contrast entity in the monitor image. Gold is particularly well suited for this application since it can be easily plated into patterns on a glass substrate such as a hood used in IR endoscopes. Additionally, if used with a nitinol, titanium or gold connection wire, the catheter iscompatible with magnetic resonance imagers. Also, rather than connecting all the lines to a common electrode, the lines could be segmented and connected to multiple electrodes. For example, a gold-patterned electrode could be constructed with four quadrants; each quadrant connected to a separate wire. Observing with the endoscope the orientation of the ablation electrode with respect to tissue would allow the physician to choose the quadrant lying against tissue and apply RF ablation only to those quadrants. Webster (U.S. Pat. No. 6,210,406) teaches a similar method using impedance as a selection method for choosing the half-hemisphere, which is lying against tissue (the higher impedance electrode has more tissue contact). The endoscope-ablation catheter would be an improvement on this impedance technique since the electrode could be oriented under direct vision to contact the endocardium. A further feature of a patterned ablation electrode is the possibility of bipolar ablation. In the above example; the ablation electrode divided into quadrants, one of the quadrants touching tissue would constitute one electrode while another segment touching the tissue could be electrically connected to function as the ground electrode.

A further advantage of constructing the ablation electrode from film deposition technology on a non-conductive substrate is the ease of constructing thermocouples on the electrode. Since thermocouples are constructed by apposition of two dissimilar metals, a thermocouple can be formed on the surface of a metallic-deposited electrode by depositing another metallic material under the electrode deposition. Moreover, multiple thermocouples can be formed on the electrode. And further, since the film of the metal forming the thermocouple may also be thin enough for optical transparency, the entire thermocouple element may be optically transparent. Or, with other imaging modalities, the thermocouple may be made so as to be transparent to the imaging energy selected.

In present ablation catheters, a thermocouple is positioned inside the platinum hemisphere electrode to measure its temperature during the ablation process. Unfortunately, the crucial temperature is the tissue temperature of which the electrode temperature is only an indirect measure. The tip warms because it's in contact with hot tissue/blood. The larger the thermal mass of the electrode, the more it can understate the temperature created at the electrode-tissue interface. In addition, the thermal mass results in a lag time between the temperature at the surface and the electrode temperature. In contrast, a surface deposited thermocouple layer has much smaller thermal mass and coupled with its proximity to the electrode surface will closely reflect the temperature at the electrode-tissue interface.

As tissue temperatures approach 100 deg C., "steam pops" can be generated. Steam pops occur because the water in the cardiac cell interior is heated past the boiling point and the cell explodes. Steam pops have been associated with endocardial dissection, a dangerous complication of RF ablation. By relying on the temperature of a conventional non-deposited electrode, the physician is uncertain when this condition occurs on the electrode surface. Moreover, metal-deposited thermocouples using the deposited electrode as one of the two metals in the thermocouple, permit multiple thermocouples to be formed, providing temperature information at multiple points on the electrode.

Instead of having separate catheters, the ablation catheter and endoscope are joined into one device—an endoscope-ablation catheter. Constructing a transparent ablation electrode with metallic film in conjunction with an endoscope has many advantages:

1. The lesion can be directly visualized during its formation. Since the lesion has different optical characteristics, the physician can watch the progression of the lesion formation and assess its suitability.
2. Coagulum and bubble formation during lesion formation can be observed and used to titrate the ablation energy. These are often harbingers of unwanted side effects such as perforation and vein stenosis.
3. Thermocouples can be easily formed on the electrode surface providing better monitoring of the crucial tissue temperature at the electrode surface.
4. Other temperature sensing technologies can be implemented such as:
    a. Infrared light. Light exceeding about 2000 nm in wavelength contains temperature information, which can be displayed to indicate the temperature at the electrode surface.
    b. Color changing chemicals. A variety of chemicals undergo color changes at different temperatures. These chemicals can be deposited on the electrode surface or imbedded in the non-metallic substrate.
5. Forming an ablation electrode with a metal deposition permits complex electrode patterns to be formed such as multiple selectable segment electrodes and bipolar electrodes.
6. Because of the small quantity of metal in metal depositions, when connected to a nitinol or gold wire, the ablation catheter becomes MR compatible
7. There is minimal motion artifact since the endoscope is pushed against the tissue. This minimizes the effect of the heart and respiratory cycles and the image produced is relatively stable.
8. The hood of the endoscope is positioned against tissue with minimal intervening blood. This minimizes blood scattering and results in high-resolution tissue images.
9. The tissue is at a fixed distance from the endoscope—the length of the hood. This distance can be chosen to provide the best perspective scene for the particular ablation performed.
10. For anatomical ablation procedures, the endoscope-ablation catheter can be positioned in precise orientations relative to tissue structures.
11. Contiguous linear lesions are easier to produce since all lesions in the field of view can be seen without being obscured by an opaque electrode. After a lesion is produced the endoscope-ablation catheter can be micropositioned adjacent to the site of the previous lesion. In this manner, any shaped contiguous line can be produced in the heart.

An additional advantage of using metal film deposition techniques for the construction of ablation electrodes is the ease of applying one or more thermocouples. Thermocouples are two dissimilar metals, which generate a voltage, which correlates to the temperature of the junction. By depositing a dissimilar metal under or over the metallic ablation material, a thermocouple is formed. Thermocouple thin films used for other applications are on the order of 100-1000 nanometers and are therefore not transparent to light. In the case of sub-100-nanometer-coated electrode, the thermocouple could be applied at one or more small areas thereby measuring the temperature at that location without significantly obscuring the image. In the case of the patterned-metallic-deposition electrode, a dissimilar metal could be applied to any of the lines composing the pattern. With this implementation, temperature could be determined at a multitude of points on the ablation electrode. Moreover, the small thermal mass of the metallic deposition and the proximity of the thermocouple close to the electrode surface would provide a more accurate and responsive temperature measurement at the tissue interface. Thermocouple thin films under 100 nanometers can also be used to create optically transparent thermocouples.

This invention may also be used with visual endoscopes as the imaging means. A conventional visual-spectrum wavelength endoscope equipped with a hood could also be used effectively to view the tissue in contact with the electrode. The infrared endoscope is more useful since it images structures through flowing blood on the periphery of the electrode. Besides viewing the tissue in contact with the endoscope, it would image tissue obscured by 1-2 cm of blood as well. So an entire 60-90 degree field of view of the ablation scene could be imaged including the catheter tip and the surrounding tissue. A visual-spectrum wavelength endoscope would only image the ablative-tissue region where the endoscope was pressed against tissue, without intervening blood. However, this would provide useful information in color of the ablative region and would be more cost-effective than the infrared endoscope. In non-blood fields where conventional endoscopes are used, a hood assembly could be attached to the endoscope. The dome-shaped tip would be coated with the metallic conductor in either a thin, transparent layer or patterned to provide transparency. Both infrared and visual-spectrum endoscopy can be employed simultaneously and selectively in the same catheter using light splitters, filters, and multiple imaging cameras in the same system.

Once the hood of the endoscope is contacting tissue, color endoscopy as well as infrared means can be used to assess the quality or suitability of the lesion and determine when adequate RF energy has been applied. Such assessment may be done by observation by a trained physician or by optical measurement means to report selected parameters such as the water content of the tissue in view indicating its degree of desiccation. Other parameters such as tissue characteristics that can be transferred optically in the visible, infrared, or other compatible region may also be monitored to add to assessment of the lesion.

It is understood that in a similar manner, a transparent metallic coating tip can be applied to any imaging transducer including intracardiac echocardiography (ICE), optical coherence tomography (OCT) devices, optical spectroscopy devices and other imaging devices. Such devices add their own unique characteristics to the ability of assessing the quality or suitability of a lesion, such as depth of penetration into the tissue. While the embodiments below are for devices employing endoscopes as the imaging means, it is obvious to one skilled in the art of medical catheters that small modifications only are needed to deposit transparent electrodes onto other imaging devices with the following design considerations:

1. Select a non-conductive substrate substantially transparent to the imaging energy employed in the imaging transducer.
2. Coat or apply this substrate over the imaging transducer.
3. Apply a transparent metallic deposition (using a coating that is transparent to the imaging energy selected or a pattern with significant open spaces).
4. Adjust the spacing of the transducer and the deposited electrode to provide high-quality imaging at the catheter interface.

For example, in an ICE catheter, the ultrasonic image is created from a rotating sector scan or an array of piezoelectric transducers to provide a longitudinal view around the catheter. In both cases, the cylindrical portion of the catheter could be covered with a substrate, which does not significantly interfere with the ultrasound transmission and then coated with a transparent metallic deposition to create the ablation electrode. This creates a cylindrical shaped ablation electrode over the imaging transducer. OCT (Optical Coherence Tomography) imaging devices employ light in an analogous manner to the ICE catheters. These catheters also image longitudinally around the catheter. Applying a non-conductive substrate over the optical window transparent to light of wavelengths 900-1300 nm and then coated with a transparent metallic deposition also create an ablation electrode over the imaging transducer. Though both of these imaging modalities currently create a longitudinal view, future forward viewing configurations if developed are subject to the same approach to create a combination imaging and ablation catheter.

Utilization of a metallic deposit as an ablation electrode has other imaging ramifications. Magnetic resonance (MR) imaging is an alternative to fluoroscopy and has many advantages including soft tissue recognition and no ionizing radiation. Unfortunately, MR imaging is incompatible with conventional ablation catheters due to the powerful magnets in the MR imager. A magnetic material such as stainless steel and platinum (used for the wire connection and electrode in conventional ablation catheters) can be moved or heated by the MR magnets. Only materials with negligible or no para or ferro-magnetism are MR-compatible. Non-magnetic materials include gold, nitinol and titanium. Copper has also been used as a wire material because of its small magnetic properties. The amount of heating and catheter movement on magnetic materials is proportional to the mass of magnetic material in the catheter. When an ablation electrode is formed by coating a non-metallic substrate with a para or ferro-magnetic coating of thickness 20-100 nm, the electrode mass is insignificant and as a result the overall magnetic properties are negligible.

DETAILED DESCRIPTION OF THE EMBODIMENTS

Figure 1:
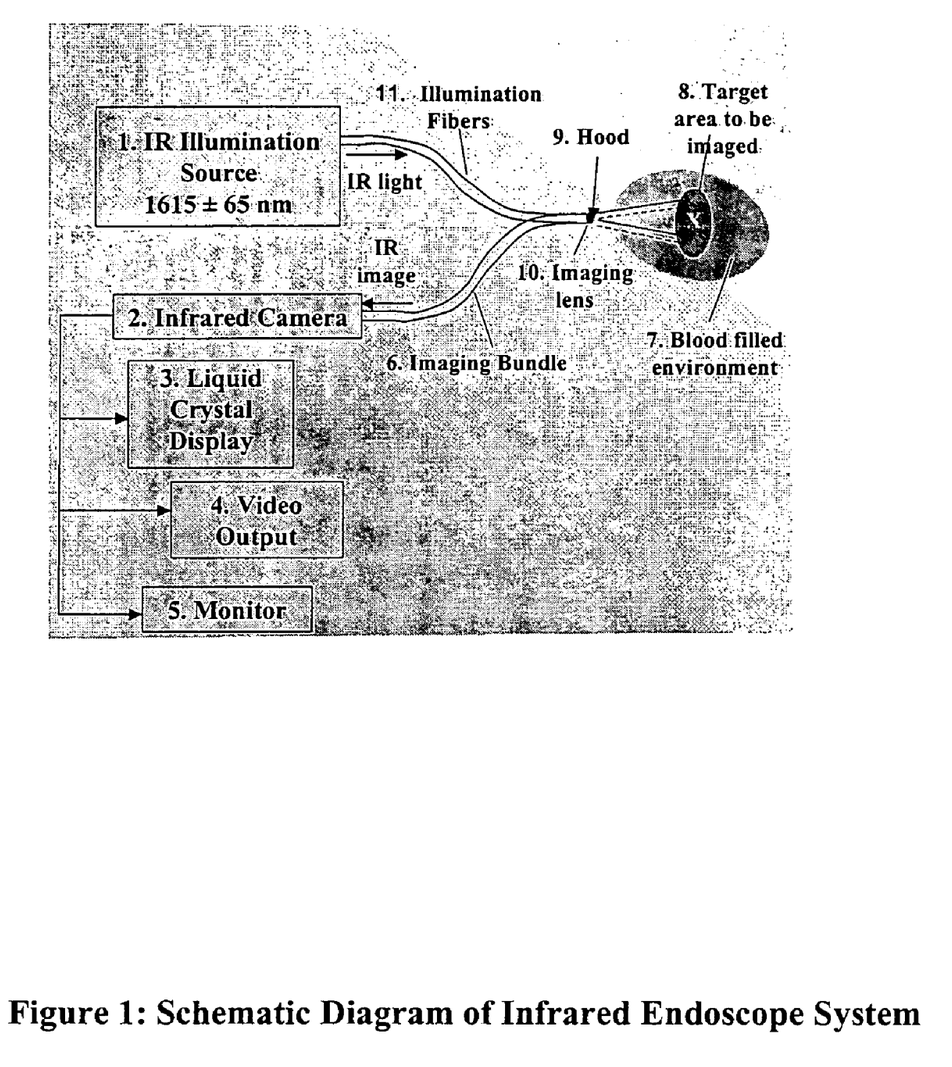
FIG. 1 is a schematic diagram of the near-infrared endoscope system.

FIG. 1 shows the near-infrared imaging endoscope system. Infrared light at a wavelength in the range 1550-1680 nm is emitted by the IR Illumination Source (1) in the form of a laser diode. The light travels down the illumination fibers (11) where it exits out of a dome-shaped glass structure and passes through the blood filled environment (7) where it illuminates a target (8). Reflections from the target pass through the blood filled environment (7), through the hood (9) into an imaging lens (10). This light is transmitted down an imaging bundle (4) until it enters the infrared camera (2). Output from the camera is sent to a video monitor (5), video output (4) and liquid crystal display (3). It is understood that the infrared camera element (2) may also incorporate various image processing means known in the art.

This system can image structures about 0.2-2.5 cm away through flowing blood. The field of view is 40-120 degrees. Pictures are displayed as black and white images and structures are displayed in real time at a frame rate of 10 frames/sec. Ablated tissue appears as a whitening of regions of the image (as reported by Knight, Heart Rhythm 2004, Abstract 26). Bubbles and coagulum formation are easily seen if they are in the field of view and within about 2 cm from the infrared endoscope (as reported by Knight, Heart Rhythm 2004, Abstract 26).

Figure 2:
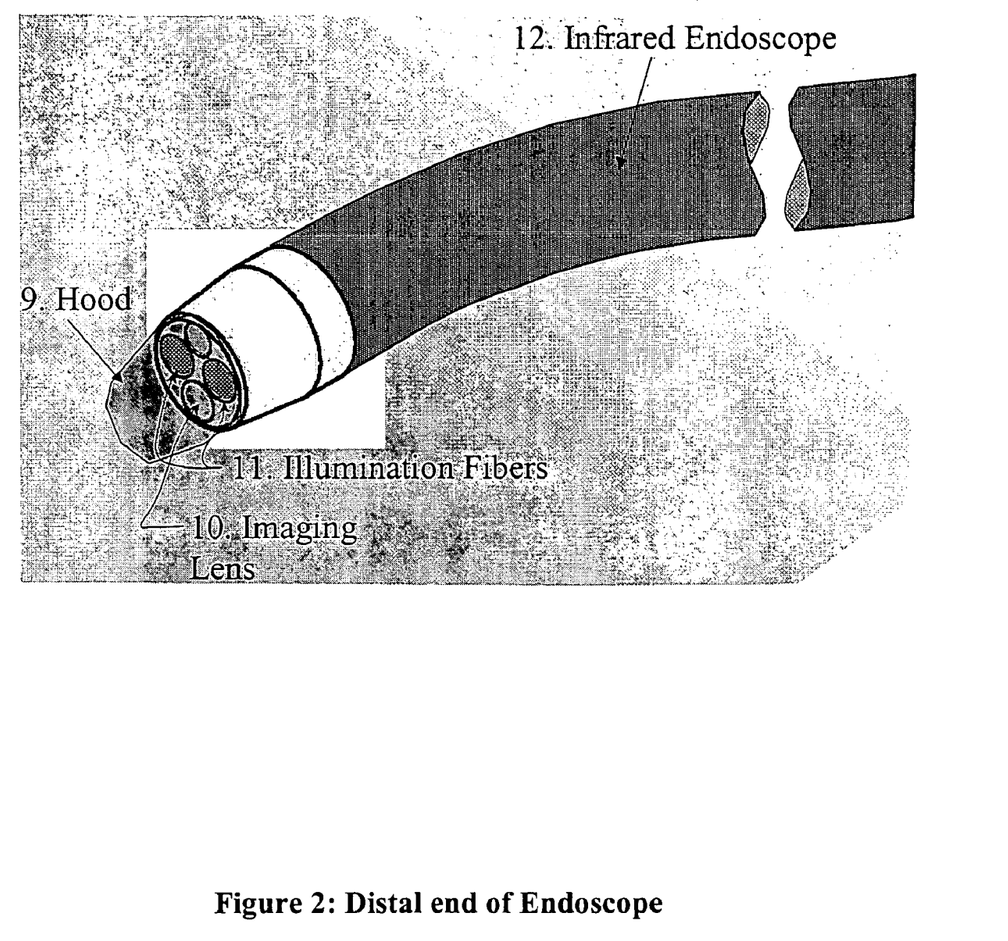
FIG. 2 is a close-up picture of the catheter distal end showing the hood configuration.

FIG. 2 shows the distal end of the infrared endoscope (12). The endoscope is about 7 French in diameter. Unlike conventional endoscopes, the infrared endoscope employs a hood (9) to reduce blood backscatter. The hood may be made of glass, silica, acrylic or various polymeric materials. The hood extends about 2 mm beyond the termination of the optical fibers.

The infrared endoscope (12) is similar in size and distal end shape to a conventional ablation catheter. By applying the radiofrequency electrode to the hood a combination endoscope-ablation catheter is formed. The ablation electrode is longer; typically it was 4 mm and more recently longer 8 mm electrodes have been introduced. Since the hood can be any size beyond about 1.5 mm in length, it could be easily extended to the 4-8 mm range. The hood (9) is also the ablation electrode if a metallic coating (14) is deposited to the surface of the hood. The disclosed embodiments inlcude an infrared imaging means or other imaging modality, although for clarity that means is not separately described.

Embodiment 1

Figure 3:
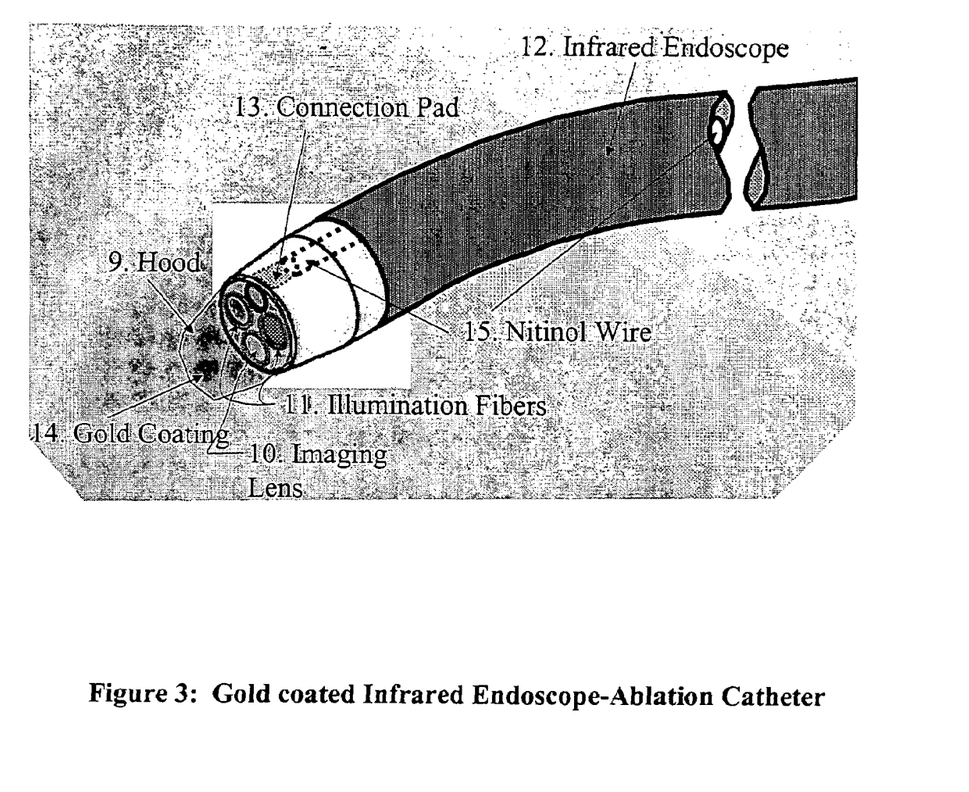
FIG. 3 is a picture of a gold-coated infrared endoscope-ablation catheter.

In FIG. 3, gold is deposited uniformly over the hood at about a 20-80 nm thickness. The gold coating is extended and attached to a gold connecting pad (13). The gold connecting pad is also electrically connected to a nitinol wire (15), which extends out of the proximal end of the catheter and is plugged into an RF generator for catheter ablation procedures. This configuration allows the physician to view the ablative process in real-time through a transparent ablation electrode.

In addition, the use of minute metallic quantities coupled with a gold, titanium or nitinol connecting wire—all non-magnetic materials—make this catheter magnetic resonance (MR) imaging compatible. Since MR machines utilize powerful magnets, conventional ablation catheters constructed from steel wires and platinum hemispheres are not only moved by the large magnets but can heat tissue from induction by the magnetic fields. With the metal-deposition process, even if a magnetic material is used, the quantity of metal in the catheter is extremely small. For example, a 4 mm long by 2.3 mm diameter hemisphere coated with 50 nm of metallic material represents a volume of about 0.0001 cubic millimeters of metal. Currently used platinum hemispheres are about 0.3-0.4 mm thick corresponding to about 10 cubic millimeters of paramagnetic metal, or about 10,000 times more metal by volume. Thus, any thin metallic deposition on a non-metallic substrate coupled with connecting wires made out of gold, nitinol or titanium will be MR-compatible. When gold, titanium or nitinol are used as the electrode deposition material, the catheter is completely MR-compatible. In an atrial fibrillation ablation, the physician positions the endoscope-ablation catheter just outside the pulmonary vein and will encircle with ablative lesions each pair of pulmonary veins. Viewing the monitor (5) in FIG. 1 during the ablation permits the physician to accurately place the electrode in a safe position relative to the pulmonary veins as well as view the entire ablation process. The lesion is seen a whitening or discoloration which grows as the RF ablation is applied. Near the end point of the ablation process, bubbles and or coagulum may appear on the monitor. These events can lead to complications and signal when the RF ablation should be terminated. Following the first lesion, if a contiguous line is desired to be produced (as in atrial fibrillation ablation) the catheter is moved to a position just adjacent to the first lesion which will appear as whitened circle on the monitor. After applying the second lesion, the physician can view both lesions to assure contiguity. In a similar manner, the physician can make a contiguous line anywhere in the heart referenced to anatomical markers, such as the pulmonary vein. Future ability to ablate while moving to create an ablation line is also contemplated.

Embodiment 2

Figure 4:
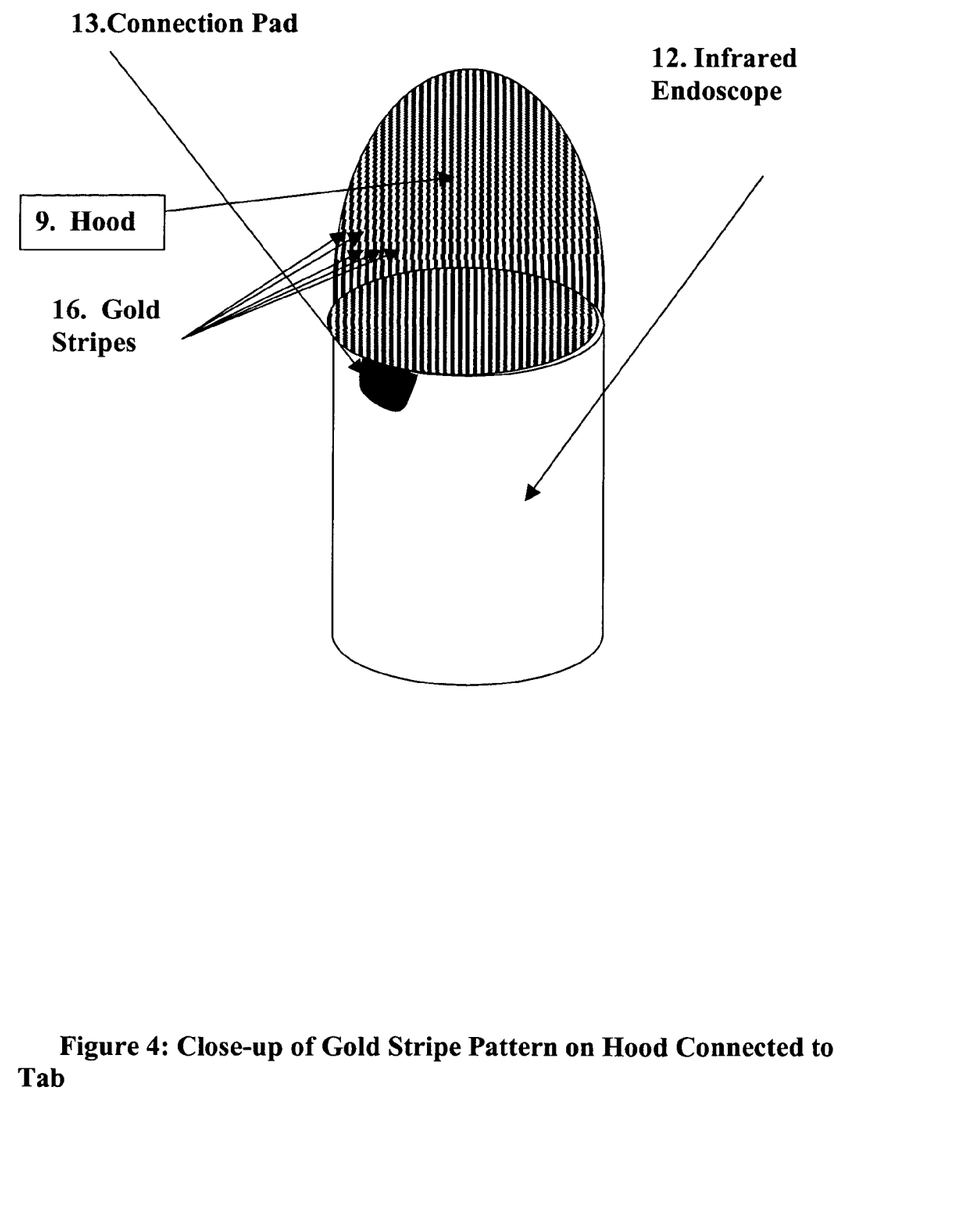
FIG. 4 is a sketch of a patterned gold coating on the hood.
Figure 5:
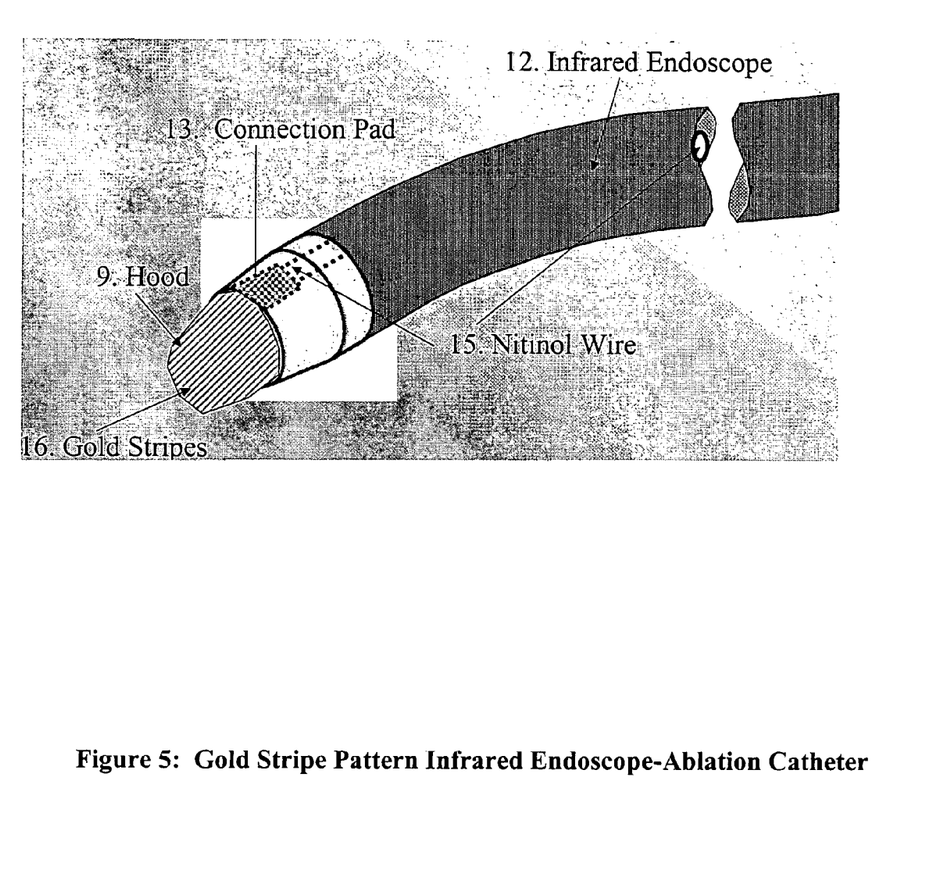
FIG. 5 is a picture of a gold-patterned infrared endoscope-ablation catheter.

An alternative to constructing a transparent electrode by coating it with a very thin layer of gold, is to form a pattern on the hood which includes enough space between the gold-deposited pattern so it appears nearly transparent on the viewing monitor. FIG. 4 shows such an embodiment. In this embodiment, a series of gold-plated stripes (16) are fabricated on the surface of the hood. Each of these stripes is connected to a gold connecting pad (13). As shown in FIG. 5, the connecting pad is connected to a nitinol, titanium or gold wire (15) for connection to an RF generator. The gold stripe does need not to be transparent since adequate imaging is provided by the spaces between the stripes. The pattern can be a cross-hatched as well as striped. The spacing between metallic lines should be no greater than one millimeter since RF energy ablates tissue about one millimeter from the electrode surface. Sub-millimeter spacings will insure a continuous lesion in the spaces between electrode stripes.

The raw image produced by the infrared camera will now include the stripes as well as tissue in the intervening spaces. By performing a SPOC in the infrared camera, the reflection from the stripes is removed. The stripe pattern would be reduced by the SPOC to a neutral contrast, leaving only the tissue as a multi-contrast entity in the monitor image. As in the first embodiment, this catheter is MR compatible if nitinol, titanium or gold connecting wires are employed.

Embodiment 3

Figure 6:
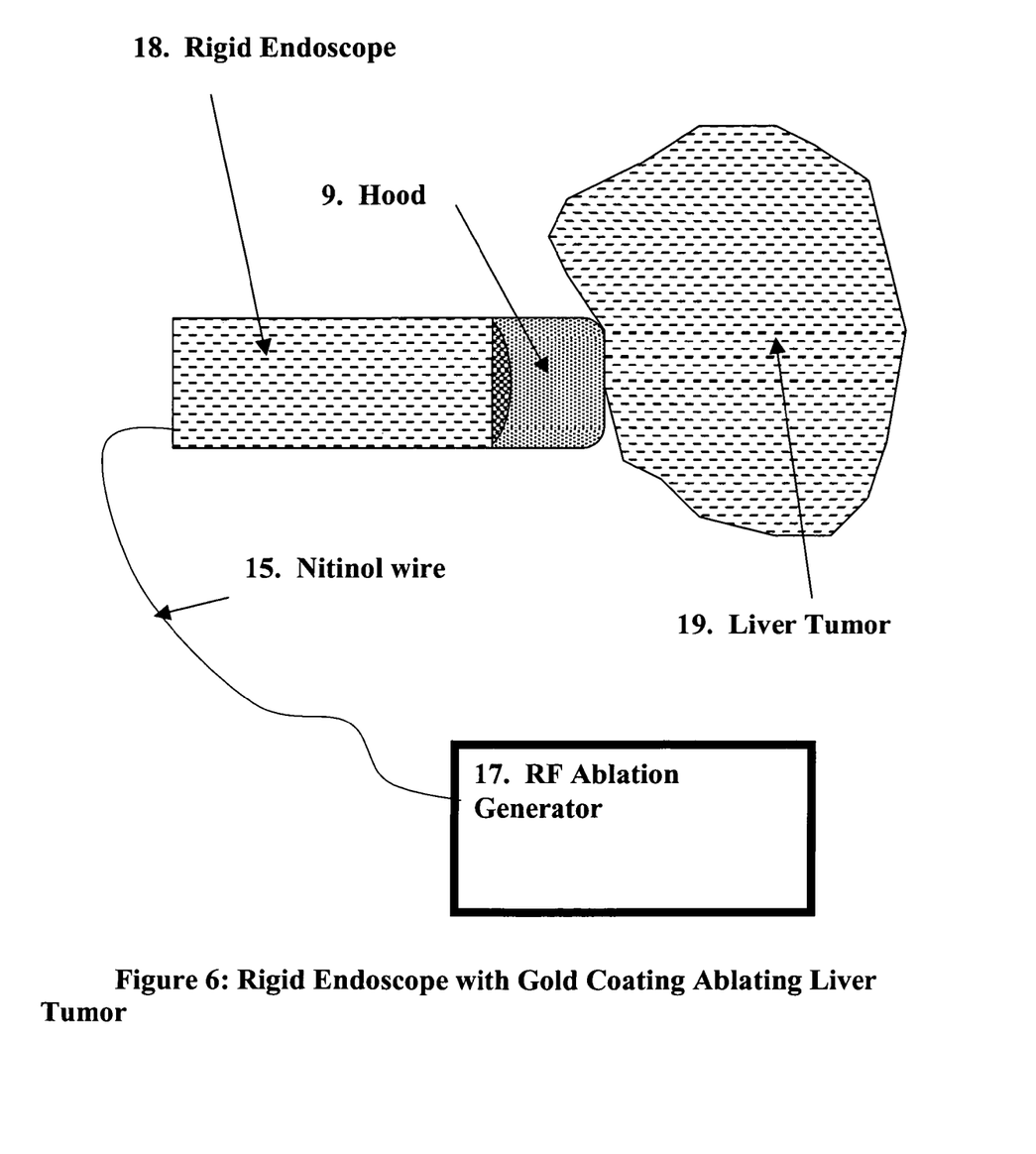
FIG. 6 is a picture of a gold-coated conventional rigid endoscope ablating a liver tumor.

A typical application of the invention is with a transvenous catheter, however the invention is not limited to that application. The next embodiment (FIG. 6) depicts a rigid conventional visible-region endoscope (18) ablating a liver tumor (19). As in the infrared endoscope, a glass hood (9) is placed over the proximal end of the endoscope. The hood is coated with a gold coating of about 60 nanometers or less. A nitinol wire connects the gold coating to an RF generator (17). The endoscope provides visual confirmation of the tumor ablation. The demarcation of the tumor boundary to normal tissue is observable in the endoscope image viewed on the monitor. This permits greater precision in eradicating the tumor with safe margins into healthy tissue to assure non-reoccurrence of the tumor.

Embodiment 4

Figure 7:
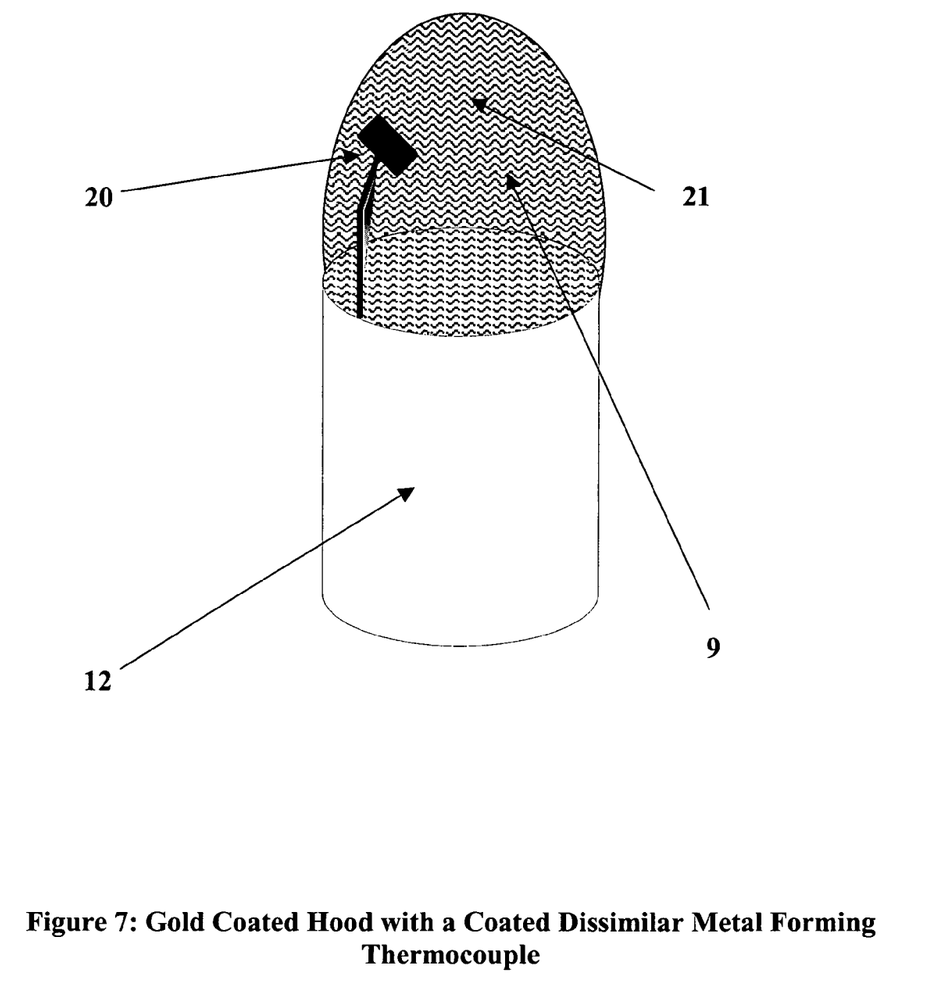
FIG. 7 is a picture of a gold-patterned infrared endoscope-ablation catheter incorporating a thermocouple.

FIG. 7 is a picture of a thin gold-coated infrared endoscope-ablation catheter incorporating a surface thermocouple. On the glass hood a thin layer of a dissimilar metal is deposited in the shape of a tab (21). This is accomplished by masking the surface except the tab shape before depositing the metal deposition. This is followed by a dissimilar metal deposition of the entire surface (20) The portions on the surface where the two dissimilar metals are in contact form a thermocouple. The two metal deposits could be any dissimilar metals. In this embodiment, gold is deposited over the tab and acts as the ablation electrode and the tab is composed of 316 stainless steel. It is connected via a nitinol wire to a radiofrequency generator. It is understood any two metals, which can be deposited can be used to form the thermocouple or the ablation electrode, and any wire type can be used to connect to the radiofrequency generator.

As in the first embodiment this embodiment uses the infrared endoscope configuration to ablate cardiac tissue. The endoscope-ablation catheter is positioned against the structure desired while viewed on the monitor. Besides viewing the underlying tissue, the position of the thermocouple will also be visible. The catheter can be maneuvered so that the thermocouple is either in contact with blood or tissue. This is accomplished by placing the endoscope-ablation catheter in an outer sheath and rotating the catheter until the thermocouple is in the desired position. The thermocouple could be positioned against tissue to accurately record the tissue temperature during ablation. Or conversely, it could be positioned against blood to insure that the critical temperature for blood coagulum formation was not exceeded. Also, multiple thermocouples could be applied on the surface to give local temperature values on various positions on the transparent electrode. In addition, a transparent thermocouple is achieved if the tab coating is in the sub-100 nm range. If transparency was achieved by the pattern-method in the second embodiment, the thermocouple material could be applied under any of the metallic lines.

Embodiment 5

Figure 8:
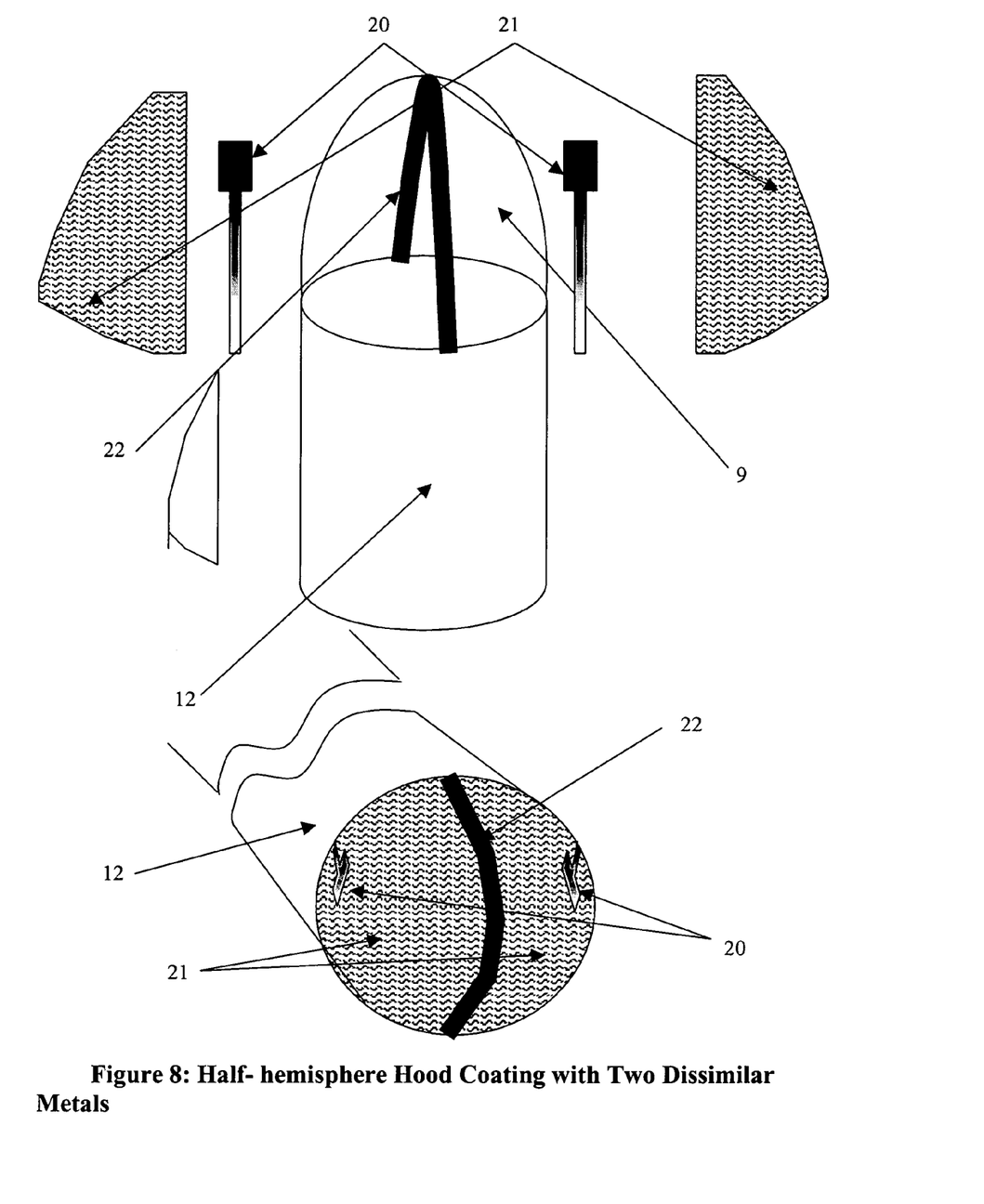
FIG. 8 is a diagram showing the application of two dissimilar metals in half-hemisphere configurations.

FIG. 8 is a diagram of how two separate half-hemisphere electrodes, each with its own thermocouple is constructed. A masking band (22) is first applied over the hood. Following this, two tabs (20) are deposited to each hemisphere with a dissimilar metal from the ablation electrode metal. Finally, the ablation metal is deposited over the entire hood. The masking band is removed and replaced with an insulating opaque material to create two half hemispheres (21) which are clearly demarcated on the monitor (FIG. 1, item 5). Each half-hemisphere (21) is connected to a separate wire routed to the distal end of the catheter, and so each half-hemisphere serves as a separate electrode. As this electrode is placed against tissue, the half-hemisphere that contacts tissue is connected to the radiofrequency generator insuring that the energy is used to ablate tissue. The half-hemisphere contacting blood would not be activated, thereby reducing the coagulum formation during the ablation. Both thermocouple wires are connected to a temperature acquisition unit, thus providing two temperature measurement places during the ablation.

Figure 9:
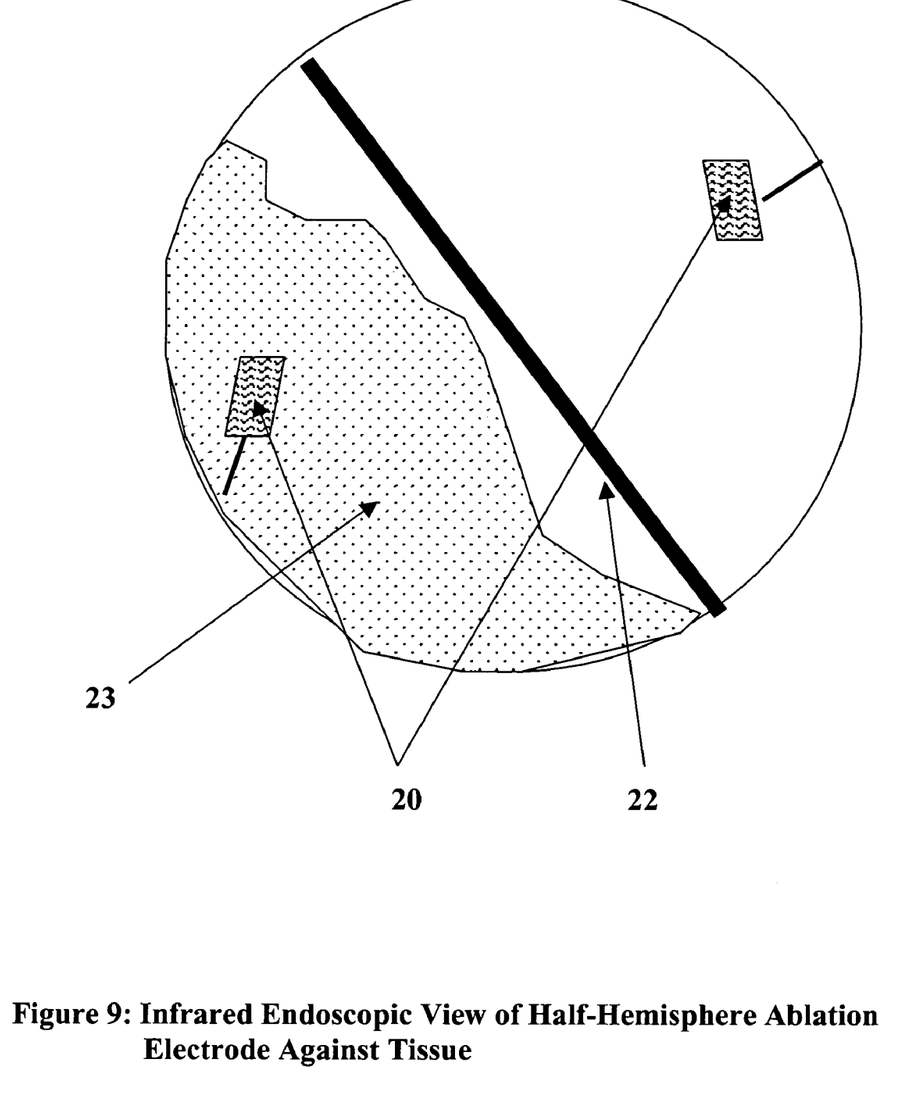
FIG. 9 is a picture showing how the ablation electrode in FIG. 8 would appear in the endoscope monitor.

In this embodiment, the temperature recorded by the two thermocouples is displayed as a color superimposed over the two thermocouples. This is accomplished in the following manner. Referring to FIG. 1, the position of the imaging bundle (6) relative to the infrared camera (2) is known because the connection is keyed to only allow insertion in one orientation. Consequently, the position of the thermocouples on the monitor (5) is also known. Over the pixels in the monitor (5) corresponding to the position of the thermocouples, a color corresponding to the temperature of the thermocouples will be displayed. As the ablation occurs, the physician now only needs to watch the monitor to fully assess the ablation and the temperature of the two thermocouples. As shown in FIG. 9, the thermocouples (21) will gradually change from green to yellow to red as the temperature increases. Bright red would correspond to a surface temperature of 100 deg C. By observing the color superimposed over the thermocouples as well as bubble and coagulum formation, the physician can quickly terminate the ablation, reducing clot formation. Fast-response active control means to adjust the ablation energy can rapidly respond to the temperature changes known to be at the tissue surface and dynamically adjust the energy applied to achieve a desired temperature set point. Such fast-response means can also be used to determine out of range conditions at blood or tissue interface points and reduce energy application to prevent steam pops and coagulum formation events.

Rather than using thermocouples to measure temperature, the use of an endoscope allows other temperature measuring means as well. The following techniques could be used as well.

1. The endoscope could incorporate a filter or beam splitter to send the component of the signal exceeding about 2000 nm to an infrared camera operating somewhere in the 2000-10000 nm range which is sensitive to heat. Different temperatures would appear as different colors. This image could be superimposed over the image of the tissue to show both tissue and temperature changes
2. The ablation electrode or substrate underneath could be coated with a chemical, which turns different colors depending on the temperature.

In both of these cases, a temperature map of the entire electrode surface would be obtained. This would be much more useful than just one or a few discrete temperature determinations. Hot spots could be recognized on the electrode surface and positional adjustments of the catheter could be made to provide more uniform heating.

An alternate ablation configuration shown in FIG. 8 is to connect the two electrodes in a bipolar radiofrequency mode. Unipolar ablation systems generally have a single electrode surface as the active ablating contact element, and utilize a large area return electrode to complete the current circuit. The return electrode is generally placed on the patient's skin. Effective operation of such systems relies on the fact that current density becomes high, and ablation occurs, only in a small region close to where the active electrode contacts tissue. Bipolar systems, on the other hand, employ two closely spaced electrodes of opposite polarity to define the current paths through tissue. The current is high because the electrodes are near to each other, and both electrodes are of comparable size, so the high current region spans the tissue volume lying between the electrodes. Bipolar electrodes may be expected to form better-defined ablation lesions, since current will not vary unexpectedly as movement of the active electrode results in changing impedance pathways to the return electrode.

Figure 10:
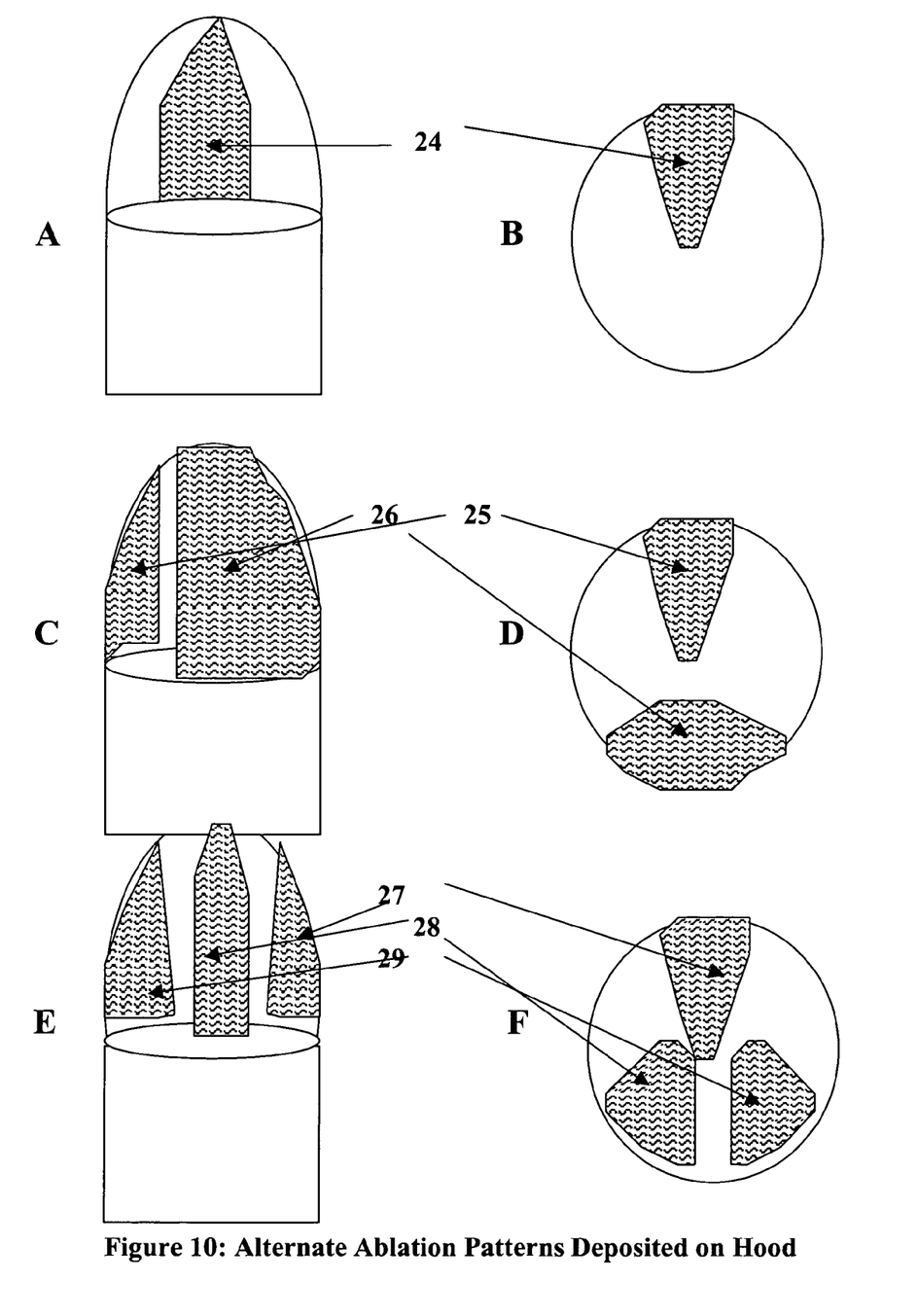
FIG. 10 show alternate electrode configurations.

Alternate electrode configurations are shown in FIG. 10. Configuration 10A and B shows the electrode from a side and top view. This configuration has one ablation segment (24) which can be rotated to position the electrode against tissue. The advantage of this approach is that the electrode is not in contact with blood and a thinner ablation line is produced. Configuration 10 C and D shows two electrodes with one electrode (25) of smaller surface area and another electrode (26) of larger surface area. The strategy is to place the smaller electrode against tissue and apply radiofrequency energy in a bipolar fashion. The smaller electrode will ablate preferentially over the larger electrode since it has smaller surface area. Configuration 10 E and F shows a tripolar configuration (26, 27, 28). Whichever electrode is lying against tissue is connected to the radiofrequency generator operating in the unipolar mode. Alternatively, this configuration could be used in a bipolar fashion. The electrode touching tissue could be one pole, and the other two could be connected as the return or ground electrode. In all of these configurations, a thermocouple could be applied to each electrode. Any number of segments could be used, such a four for a quadrant configuration described previously, or more if desired.

In summary (and without limitation), this invention teaches the following methods and means:

1. A transparent ablation electrode whereby the underling tissue can be viewed by an endoscope during the ablation using metallic film deposition technology applied to transparent non-metallic substrate. This is accomplished by coating a transparent non-metallic substrate (such as glass or silica) with a metal deposition thin enough to see through or by applying a pattern with sufficient open spaces to see the underlying tissue.

2. Forming a thermocouple on the electrode surface using the electrode surface as one of the thermocouple metals. Constructing thermocouples in this manner improves the accuracy and provides fast time response to the tissue/blood temperature. It also provides an easy means to create multiple thermocouples on the electrode surface.

3. Displaying temperature information in a user-friendly format. Temperature is displayed as color changes on the endoscope monitor. This permits all crucial information during the ablation to be displayed on one monitor 4. Alternate temperature measurements apart from thermocouples in conjunction with an endoscope. One alternate method is to view the emitted light in the 2000-10,000 nm region. Another is to coat the electrode or substrate with chemical whose color changes with temperature.

5. Constructing complex electrode patterns on the ablation electrode surface to create alternate ablation patterns in conjunction with an endoscope. Selection of electrode segments seen to be lying against tissue are taught in the embodiments.

6. Using the bipolar mode of radiofrequency application with one electrode segment being one pole while one or more segments forms the other pole.

7. Constructing a magnetic resonance imaging compatible ablation catheter using thin metallic depositions on a non-metallic substrate connected to a gold, titanium or nitinol wire routed to the catheter distal end.

8. Using fast response dynamic control of energy applied to take advantage of the fast time response to temperature of the ultra-low thermal mass electrodes and thermocouples or infrared light measured temperature in order to control to a predetermined tissue temperature set point.

9. Using fast response means to reduce energy applied to prevent steam pops or coagulum formation events at tissue and/or blood contact surfaces.

We claim:

1. A radio frequency ablation electrode constructed on an imaging catheter having an indwelling imaging device oriented to image tissue near or at the distal end of the catheter, comprising:
   a) a non-conductive substrate applied to the imaging device, the substrate being transparent to the imaging device;
   b) a conductive coaling or pattern is deposited on the substrate;
   c) a wire connecting the conductive coating or pattern to an RF ablation generator whereby the ablation is produced and imaged
   where the coating is sufficiently thin to permit substantial transmission through the coating for the energy transmitted by the imaging device.

2. A device according to claim 1 where the catheter is transvenous.

3. A device according to claim 1 where the tissue is heart tissue.

4. A device according to claim 1 where the conductive coating is metallic.

5. A device according to claim 4 where the metallic coating is gold.

6. A device according to claim 1 where the coating is an open pattern on the imaging transducer.

7. A device according to claim 1 where the imaging device is an infrared endoscope.

8. A device according to claim 1 where the imaging device is an ICE catheter.

9. A medical catheter assembly comprising:
   (a) a radio frequency ablation electrode;
   (b) an imaging assembly for viewing a position distally forward or proximally displaced and angled outward toward a tissue, the imaging assembly having operational wavelengths, the imaging assembly further having an outside viewing surface, the ablation electrode being on the outside viewing surface;
   (c) the imaging assembly's outside viewing surface being a nonconductive or a semi-conducting substrate material applied to a distal end of the imaging assembly, and the substrate is substantially transparent to the operational wavelengths of the imaging assembly;
   (d) a thin conductive coating or pattern deposited on the substrate material that is substantially transparent to the operational wavelengths of the imaging assembly; and
   (e) a conductive connection or wire attached to the conductive coating or pattern to allow radio frequency energy for ablation of the tissue under the view of the imaging assembly.

* * * * *